United States Patent [19]

Johnson et al.

[11] 4,014,919
[45] Mar. 29, 1977

[54] PROCESS FOR PREPARING METHYL JASMONATE AND RELATED COMPOUNDS

[75] Inventors: Francis Johnson, Setauket, N.Y.; Kenneth G. Paul, West Newton, Mass.; Duccio Favara, Como, Italy

[73] Assignee: The Dow Chemical Company, Midland, Mich.

[22] Filed: Mar. 1, 1974

[21] Appl. No.: 447,101

[52] U.S. Cl. .............................. 260/468 K; 260/483
[51] Int. Cl.$^2$ .................. C07C 69/74; C07C 67/30
[58] Field of Search ................... 260/468 K, 514 K

[56] References Cited
OTHER PUBLICATIONS

House, Modern Synthetic Reactions, 2nd Ed. pp. 756–761 (1973).
Ireland et al., JACS 81, 2907 (1959).
House, Modern Synthetic Reactions, 2nd Ed. pp. 10, 14, 516–518, 641–643, 762–765 (1973).
March, Advanced Organic Chem. pp. 350–361, 364, 477–481, 592–596, 642–645 (1969).

*Primary Examiner*—Robert Gerstl
*Attorney, Agent, or Firm*—Theodore Post; C. Kenneth Bjork

[57] ABSTRACT

Methyl dl-jasmonate and related compounds, which are useful in perfumery, are synthesized by alkylation of a 2-carbo(lower alkoxy)-3-oxocyclopentaneacetic acid lower alkyl ester. A new method for the synthesis of the intermediates, 2-carbo(lower alkoxy)-3-oxocyclopentene-1-acetic acid lower alkyl esters, is also described.

3 Claims, No Drawings

PROCESS FOR PREPARING METHYL JASMONATE AND RELATED COMPOUNDS

BACKGROUND OF THE INVENTION dl-Methyl jasmonate is an ingredient of jasmine oil which is used for preparing perfume compositions and has the following structure

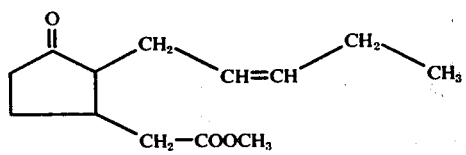

wherein the stereochemistry of the two aliphatic substituents on the cyclopentanone ring is trans. The 2-pentenyl double bond has the cis-configuration.

Syntheses of methyl jasmonate and of related 2-alkyl- and 2-alkenyl-3-oxo-cyclopentaneacetic acid lower alkyl esters have been reported in the chemical literature; E. Demole et al., Helv. Chim. Acta, 45, 692 (1962); K. Sisido et al., J. Org. Chem. 34 (9), 2661 (1969); Belgian Patents Nos. 628,779 and 791,801; and Swiss Patent No. 490,313.

SUMMARY OF THE INVENTION

A new synthetic route has now been discovered for methyl jasmonate and related compounds of 3-oxo-cyclopentaneacetic acid of the formula

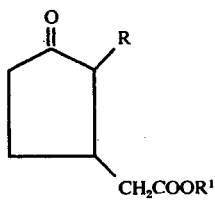

wherein R represents an alkenyl radical of 4 to 6 carbon atoms, i.e., of the group butenyl, pentenyl and hexenyl and $R^1$ is methyl or ethyl. The process is a multi-step synthesis involving the preparation as intermediates of 2-carbo(lower alkoxy)-3-oxo-cyclopentene-1-acetic acid lower alkyl esters, the subsequent hydrogenation of the cyclopentene ring to cyclopentane, alkylation at position 2 with a haloalkyne and elimination of the 2-carbo(lower alkoxy) group. Catalytic hydrogenation of the alkynyl substituent to an alkenyl radical affords compounds of formula I. The present process is more easily carried out and gives better yields than previous methods of synthesis. The compounds are useful in perfumery.

DESCRIPTION OF THE PREFERRED EMBODIMENTS

The series of reactions involved in the synthesis is represented by the following scheme:

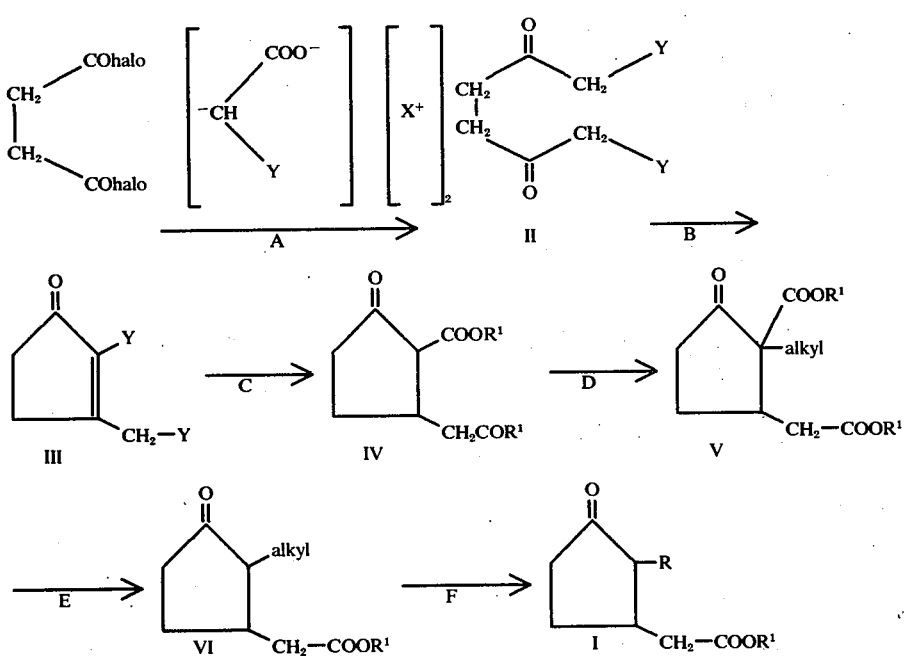

STEP A

As the starting material of the process, a succinoyl chloride, bromide or iodide may be employed. For example, substantially one molar proportion of succinoyl chloride is added to substantially four molar proportions of a di-salt of the formula indicated above the arrow, wherein Y represents a —$COOR^1$ group and wherein $R^1$ is methyl or ethyl and $X^+$ represents an alkali metal cation or a monovalent magnesium cation selected from the group of $MgBr^+$, $MgCl^+$ and $MgI^+$. The temperature of the reaction may vary from $-30°$ to $++°$ C. The solvent is advantageously an appropriate anhydrous inert organic solvent such as, for example, a lower alkyl ether, dioxane or tetrahydrofuran. The resulting reaction product, compound II, is recovered by removing the solvent under high vacuum.

STEP B

This step involves the intramolecular cyclization of compound II, which is preferably carried out in alkaline media. To obtain the cyclopentenone, compound III, the diketone II is stirred at 0° to 30° C for 0.5 to 2 hours with dilute aqueous base such as, for example, 0.1N alkali metal hydroxide. The cyclopentenone is recovered by acidification of the reaction mixture to a pH of about 3, followed by extraction with a water-immiscible organic solvent. Evaporation of the solvent gives the desired product, compound III.

STEP C

This step involves the reduction of the double bond of the cyclopentene ring of compound III. A reducing agent advantageously employed in step C is hydrogen gas in the presence of a noble metal or a noble metal oxide as the catalyst. For example, Pd supported on barium sulfate or charcoal or $PtO_2$ poisoned with a trace of pyridine gives excellent results. The hydrogenation is usually carried out in an inert organic solvent such as, for example, benzene or ethyl acetate at room temperature and at a pressure ranging from substantially atmospheric pressure to substantially 5 atmospheres. Other reducing systems may be employed in this step such as, for example, zinc in acetic acid, without substantially affecting the yield.

STEP D

To introduce the aliphatic substituent R in position 2 of the cyclopentanone ring, the compound IV obtained pursuant to step C is first reacted with an alkylating agent of the formula alkyl—X wherein the portion "alkyl" identifies an aliphatic radical of 4 to 6 carbon atoms containing a triple bond, e.g., butyne, pentyne or hexyne, and X is a good leaving group such as, for example, Cl, Br, $ONO_2$, tosylate, mesylate and the like. Examples of alkylating agents include the following: 1-bromo-3-butyne, 1-bromo-2-butyne, 1-bromo-2-pentyne, 1-chloro-2-pentyne, 1-tosyloxy-3-pentyne, 1-chloro-4-pentyne, 1-mesyloxy-2-hexyne, 1-bromo-2-hexyne, 1-bromo-3-hexyne.

In a preferred method, the alkylation is carried out on an alkali metal salt of the cyclopentanone compound which is obtained, for example, by reacting an alkali metal hydride with the cyclopentanone compound. The alkylating agent is contacted with the cyclopentanone salt in the presence of an inert organic solvent at a temperature ranging from about 20° to 30° C. Among such solvents, which may be employed advantageously, mixtures of benzene and dimethylformamide give excellent results.

STEP E

The compound V obtained pursuant to step D still contains a carbo(lower alkoxy) substituent at position 2 of the cyclopentane ring which must be eliminated at this stage. The elimination may be performed by heating the cyclopentanone diester with sodium chloride or similar salts in wet dimethyl sulfoxide at 140 to 190° C, pursuant to the method of P. Krapcho et al., Tetrahedron Letters No. 12, 957, 1973. The compound obtained is a methyl or ethyl ester of 2-alkynyl-3-oxocyclopentaneacetic acid.

An alternative procedure involes refluxing the cyclopentanone diester in collidine with lithium iodide dihydrate to give a 2-alkynyl-3-oxocyclopentaneacetic acid which is converted to the corresponding methyl or ethyl ester, conveniently by reaction with a methyl or ethyl halide in dimethyl acetamide in the presence of a hydrogen halide acceptor. Other well known esterification methods may be suitably employed. The alternative procedures for removing the carbo(lower alkoxy) substituent at position 2 of the cyclopentane ring will be referred to sometimes as "eliminating" said group.

STEP F

Hydrogenation of the triple bond in the side chain of compound VI to a double bond affords compound I, wherein R is a $C_4$-$C_6$ alkenyl group. The selective hydrogenation to a cis-olefin may be achieved by operating at low pressure, preferably at atmospheric pressure, and room temperature and employing palladium catalysts modified by transition metal salts such as the Lindlar catalyst or better by a supported palladium catalyst deactivated with a nitrogen base such as pyridine or quinoline.

The following additional description and examples further describe the invention and the manner and process of making and using it to enable the art skilled to make and use the same and set forth the best mode contemplated by the inventors of carrying out the invention.

EXAMPLE 1

To 25 g. of magnesium in 600 ml. of dry tetrahydrofuran containing an iodine crystal, 123 g. of isopropyl bromide is added at such a rate as to keep the reaction mixture gently refluxing. When all the halide has been added, stirring and refluxing are continued for 20 minutes. The reaction mixture is then cooled to room temperature and 2000 ml. of dry tetrahydrofuran is added. Then 156 g. (1 mole) of potassium methyl malonate is added in 20 minutes from a dropping funnel suitable for solids and the reaction mixture is then refluxed for 1 to 2 hours. After cooling the reaction mixture to room temperature, 38.75 g. (0.25 mole) of succinoyl chloride is added over a 15 minute period. The reaction mixture is then stirred at room temperature overnight. The reaction mixture is then poured into a vigorously stirring mizxture of 70 ml. of concentrated $H_2SO_4$ in 700 ml. of ice and water. The organic layer is separated and the aqueous layer is extracted with three portions of ether. The aqueous layer is then discarded. The combined organic extracts are washed with aqueous saturated sodium bicarbonate, then with brine. After drying ($MgSO_4$), the solvent is evaporated, leaving 44 g. of fairly pure dimethyl 3,6-dioxosuberate (an oil). Yield 76.5%; spectral data are consistent with the assigned structure.

EXAMPLE 2

To 43.8 g. (0.19 mole) of dimethyl 3,6-dioxosuberate a 1N solution of NaOH (195 ml., 0.195 mole) is added over a 30 minute period with stirring and ice cooling. After the addition is complete, the ice bath is removed and stirring is continued for half an hour. The reaction mixture is then poured into water (100 ml.) and extracted three times with 50 ml. of ethyl acetate which is then discarded. 2N HCl is added to the aqueous solution (to pH 3) and the solution is extracted three times with 200 ml. of ethyl acetate. The combined organic extracts are washed with brine, dried ($MgSO_4$) and the solvent evaporated. 34.2 Grams of the methyl ester of 2-carbomethoxy-3-oxocyclopentene-1-acetic acid remains in the flask (84%). Spectral data are in agreement with the above structure.

EXAMPLE 3

To 0.5 g. of palladium on carbon under nitrogen, a solution of 5 g. (0.0236 mole) of the methyl ester of 2-carbomethoxy-3-oxocyclopentene-1-acetic acid in 60 ml. of ethyl acetate is added and the mixture is hydrogenated at atmospheric pressure and room temperature. The reaction is completed in about 20 minutes. The catalyst is then filtered off and the solvent evaporated, giving 5 g. of an oily product which is distilled at 90°–100° C/0.2 mm Hg. The yield of the methyl ester of 2-carbomethoxy-3-oxo-cyclopentaneacetic acid is practically quantitative. N.M.R. and I.R. data are in agreement with the assigned structure.

The homolog 2-carbethoxy-3-oxo-cyclopentaneacetic acid ethyl ester (compound IV, $R^1$=ethyl) is prepared pursuant to the procedure followed in the previous examples, except that in the procedure of Example 1 potassium ethyl malonate is employed instead of potassium methyl malonate.

EXAMPLE 4

A 57% dispersion of sodium hydride in oil (0.775 g., corresponding to 0.0184 mole of sodium hydride) is washed twice in a dry flask with 15 ml. of hexane under nitrogen to remove the oil. After the hexane has been removed with a pipette, 20 ml. of a 1/1 mixture of dimethylformamide-benzene is added and the resulting slurry cooled to 0°–5° C. 3.935 Grams of the methyl ester of 2-carbomethoxy-3-oxo-cyclopentaneacetic acid (0.0184 mole) is then added dropwise in 4 ml. of dimethyl formamide/-benzene 1/1. The reaction mixture is left under stirring at room temperature for 5 minutes then 2.96 g. of 1-bromo-2-pentyne (0.02 mole) is added dropwise. After 3 hours, the pH is only slightly basic (8–9). The reaction mixture is poured into water and extracted twice with ether. The aqueous phase is discarded and the ether layer washed with water, dried (MgSO$_4$) and evaporated. The resulting liquid is kept under reduced pressure (water pump) at 100° C for 1 hour to remove any traces of unreacted 1-bromo-2-pentyne. There is obtained 4.6 g. of a colorless oil which solidifies on standing; m.p. 49°–50° C. I.R. and N.M.R. are consistent with the methyl ester of 2-carbomethoxy-3-oxo-2-(2-pentynyl)-cyclopentaneacetic acid. Yield 89.3%. A sample recrystallized from hexane has an m.p. of 50°–51° C.

Anal., percent: Calculated: C, 64.26; H, 7.19. Found: C, 64.15; H, 7.15.

The corresponding compound wherein the methyl groups are replaced by ethyl is obtained essentially according to the procedure described above by using as the starting material compound IV wherein $R^1$ is ethyl. The alkylation of compounds of formula IV with different alkylating agents such as those listed before is carried out essentially according to the method described in this example. The following compounds of formula V are so obtained:

2-(3-butynyl)-2-carbomethoxy -3-oxo-cyclopentaneacetic acid methyl ester 2-(2-butynyl)-2-carbomethoxy-3-oxo-cyclopentaneacetic acid methyl ester 2-carbomethoxy-3-oxo-2-(4-pentynyl)-cyclopentaneacetic acid methyl ester 2-carbethoxy-3-oxo-2-(2-pentynyl)-cyclopentaneacetic acid ethyl ester 2-carbethoxy-2-(3-hexynyl)-3-oxo-cyclopentaneacetic acid ethyl ester 2-carbomethoxy-2-(2-hexynyl)-3-oxo-cyclopentaneacetic acid methyl ester.

EXAMPLE 5

3.1 Grams (0.0182 mole ) of lithium iodide dihydrate is dissolved in 12 ml. of dry collindine under nitrogen by heating at about 80° C. Then 1.70 g. of the methyl ester of 2-carbomethoxy-3-oxo-2-(2-pentynyl)-cyclopentaneacetic acid (0.0061 mole) in 3 ml. of collidine is added dropwise thereto. The reaction mixture is refluxed for 10 hours, after which time carbon dioxide evolution becomes very slow. The reaction mixture is then cooled and poured into ether and water and the organic layer separated. The aqueous layer is washed three times with ether and the combined ether layers are set aside. The aqueous layer is acidified with 2N HCL and extracted three times with ether which, after being washed with brine, is dried (MgSO$_4$) and evaporated, leaving 0.892 g. of 3-oxo-2-(2-pentynyl)-cyclopentaneacetic acid, a very viscous oil. Yield 71%. Spectroscopic properties are in agreement with the assigned structure. Its 2,4-dinitrophenylhydrazone melts at 173°–174° C.

Two grams (0.009615 ml.) of the acid obtained as described above is added to 10 ml. of freshly distilled dimethyl acetamide followed by 1 g. of sodium bicarbonate (0.012 mole) and 1.2 ml. of methyl iodide (0.0192 mole). The reaction mixture is stirred at room temperature in the dark in a closed flask for 24 hours. The reaction mixture is then poured into ether and the ether washed 5 times with water. After drying, the ether is evaporated, leaving 1.90 g. of methyl ester of 2-carbomethoxy-3-oxo-(2-pentynyl)-cyclopentaneacetic acid. Yield 89%. Spectral data are in agreement with the proposed structure. The product was characterized as its semicarbazone, m.p. 168°–169° C.

The same methyl ester may be obtained directly from compound V wherein $R^1$ is methyl by cleavage with sodium chloride in wet dimethylsulfoxide at a temperature ranging from about 140° to 190° C.

EXAMPLE 6

Four hundred mg. of the methyl ester of 3-oxo-2-(2-pentynyl)-cyclopentaneacetic acid dissolved in 10 ml. of pyridine is added to 100 mg of 5% palladium on barium sulfate, and the resulting mixture is hydrogenated at room temperature and pressure. Forty-four milliliters of hydrogen is absorbed in 90 minutes, then the reaction stops completely. After filtering off the catalyst, the solvent is evaporated. The remaining oil is dissolved in ether-hexane 1:1 and washed with 1N HCl, aqueous saturated sodium bicarbonate and finally water. After drying (MgSO$_4$), the solvent is evaporated and 392 mg. of methyl cis-jasmonate is obtained. Yield 98%. Spectral properties are in agreement with the above structure and published spectral data. The product shows one spot on thin layer chromatography. Methyl cis-jasmonate was also characterized as its semicarbazone, m.p. 118°–119° C (Lit. 115°–117° C).

Anal., percent: Calculated: C, 59.76; H, 8.24; N, 14.94. Found: C, 59.74; H, 8.25; N, 14.77.

From the compound outlined in Example 4, pursuant to procedures as described in Exampls 5 and 6, the following compounds can be prepared:

2-(3-butenyl)-3-oxo-cyclopentaneacetic acid methyl ester 2-(2-butenyl)-3-oxo-cyclopentaneacetic acid methyl ester 3-oxo-2-(4-pentenyl)-cyclopentaneacetic acid methyl ester 3-oxo-2-(2-pentenyl)-cyclopentaneacetic acid ethyl ester 2-(3-hexenyl)-3-oxo-cyclopentaneacetic acid ethyl ester 2-(2-hexenyl)-3-oxo-cyclopentaneacetic acid methyl ester.

The 2-alkenyl-3-oxo-cyclopentaneacetic acid lower alkyl esters so prepared have a jasmine-like fragrance and are therefore useful in perfumery.

That which is claimed is:

1. A process for preparing a 3-oxo-cyclopentaneacetic acid derivative represented by following formula I

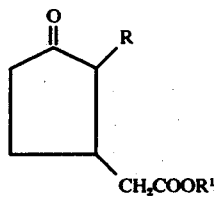

wherein R represents an alkenyl radical of 4 to 6 carbon atoms wherein the unsaturation is in the 2-, 3- or 4-position and $R^1$ is methyl or ethyl, which comprises the following steps: (A) mixing at a temperature between about −30° and +30° C in an inert organic solvent substantially one molar proportion of a succinoyl halide with substantially four molar proportions of a salt represented by the formula

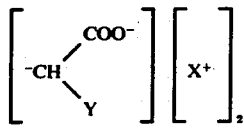

wherein Y represents A $COOR^1$ group wherein $R^1$ represents methyl or ethyl, $X^+$ represents an alkali metal cation or a monovalent magnesium cation selected from the group $MgBR^+$, $MgCl^+$ and $MgI^+$, pouring the reaction mixture into a vigorously stirred mixture of an excess of concentrated mineral acid, ice and water, separating the organic layer, washing it free of excess mineral acid with aqueous concentrated alkali metal bicarbonate and drying and recovering the said reaction product, a diketo compound represented by following formula II

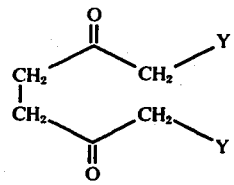

wherein Y has the meaning previously given; (B) mixing compound II in aqueous alkaline medium at about 0° to 30° C for about 0.5 to 2 hours to cyclize compound II to form the corresponding 3-oxo-1-cyclopenteneacetic acid derivative; (C) reducing the cyclopentene ring of the last-named compound with hydrogen in the presence of a noble metal or a noble metal oxide as the catalyst to give the corresponding cyclopentane derivative; (D) alkylating the so-obtained 3-oxo-cyclopentaneacetic acid derivative at position 2 with a compound of the formula alkynyl-X wherein "alkynyl" represents a $C_4$–$C_6$ aliphatic chain containing a triple bond in the 2-, 3- or 4- position and X represents a leaving group selected from Cl, Br, $ONO_2$, tosylate and mesylate, to give a compound of following formula V

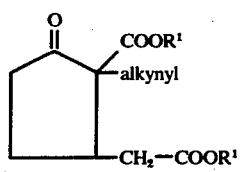

wherein $R^1$ and alkynyl have the meaning previously given; (E) eliminating the $COOR^1$ group at position 2 of the cyclopentanone ring; and (F) selectively hydrogenating the alkynyl group to a cis- olefin group by means of hydrogen gas at substantially room temperature and substantially atmospheric pressure in the presence of a palladium catalyst and recovering the product.

2. A compound represented by the formula

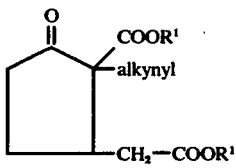

wherein $R^1$ represents methyl or ethyl and alkynyl represents a $C_4$ to $C_6$ aliphatic radical containing a triple bond in the 2-, 3- or 4- position.

3. The compound of claim 2 which is 2-carbomethoxy-3-oxo-2-(2-pentynyl)-cyclopentaneacetic acid methyl ester.

* * * * *

UNITED STATES PATENT AND TRADEMARK OFFICE
CERTIFICATE OF CORRECTION

PATENT NO. : 4,014,919
DATED : March 29, 1977
INVENTOR(S) : Francis Johnson et al.

It is certified that error appears in the above-identified patent and that said Letters Patent are hereby corrected as shown below:

Title page, right hand side, second line, "14,516-518 should read -- 19,516-518, --;

and in the third line, "pp. 350-361," should read -- pp. 357-361, --.

Column 2, line 59, "++°C." should read -- +30°C. --.

Column 2, line 57, "MgBR$^+$" should read -- MgBr$^+$ --.

Column 3, line 64, "involes" should read -- involves --.

Column 4, line 27, after "magnesium", insert the omitted word -- turnings --; and on line 42, "mizxture" should read -- mixture --.

Column 5, line 18, "exampls," should read -- examples --.

Column 6, line 6, "collindine" should read -- collidine --;

line 17, "2N HCL" should read --2N HCl --; and on line 63, "exampls" should read examples --.

UNITED STATES PATENT AND TRADEMARK OFFICE
CERTIFICATE OF CORRECTION

PATENT NO. : 4,014,919
DATED : March 29, 1977
INVENTOR(S) : Francis Johnson et al.

It is certified that error appears in the above-identified patent and that said Letters Patent are hereby corrected as shown below:

Column 7, line 50, "MgBR$^+$" should read -- MgBr$^+$ --.

Signed and Sealed this

First Day of November 1977

[SEAL]

Attest:

RUTH C. MASON
*Attesting Officer*

LUTRELLE F. PARKER
*Acting Commissioner of Patents and Trademarks*